United States Patent [19]
Hsiao

[11] Patent Number: 5,749,836
[45] Date of Patent: May 12, 1998

[54] QUANTITATIVE SKIN ALLERGIC TEST DEVICE

[76] Inventor: Ray-Ling Hsiao, 4F, No. 12, Alley 15, Lane 175, Sec. 2, Ho-Ping East Rd., Taipei, Taiwan

[21] Appl. No.: 621,939

[22] Filed: Mar. 26, 1996

[51] Int. Cl.⁶ .................................................. A61B 5/04
[52] U.S. Cl. ............................................................ 600/556
[58] Field of Search ................................ 128/743; 604/43, 604/46

[56] References Cited

U.S. PATENT DOCUMENTS

| | | | |
|---|---|---|---|
| 3,556,080 | 1/1971 | Hein | 128/743 |
| 4,237,906 | 12/1980 | Harstad et al. | 128/743 |
| 4,607,632 | 8/1986 | Brennan et al. | 128/743 |
| 4,802,493 | 2/1989 | Meganias | 128/743 |
| 5,538,134 | 7/1996 | Pitesky | 128/743 |

*Primary Examiner*—Max Hindenburg
*Attorney, Agent, or Firm*—W. Wayne Liauh

[57] ABSTRACT

The present invention relates to an improved quantitative skin allergic test device, which has a finger grip to be held by fingers; a cover having a sealing plug portion adaptful for the mouth of an antigen container; an elongated stem, extending from the sealing plug portion, formed with a raised portion at the end thereof; and a plurality of punctures, provided at the end of the elongated stem, being capable of carrying sufficient antigen liquid to conduct the test. The raised portion may be act as a stop to limit excessive penetration of the punctures, therefore preventing the epidermis layer of the skin of a patient from being penetrated while conducting a skin allergic test so as to obtain an accurate interpretation of the test result.

3 Claims, 5 Drawing Sheets

5,749,836

QUANTITATIVE SKIN ALLERGIC TEST DEVICE

FIELD OF THE INVENTION

The present invention relates to a quantitative skin allergic test device, and, more particularly to an improved quantitative skin allergic test device capable of limiting excessive penetration of the punctures thereof to prevent the epidermis layer of the skin of a patient from being penetrated.

BACKGROUND OF INVENTION

For a skin allergic test, the allergic test conducted by a skin test device of puncture type is one of the most common ways at present. One example of such a device, as shown in FIG. 1, comprises a finger grip (A), an elongated stem (B) extending therefrom, and a plurality of punctures (C) attached to the end of the elongated stem (B). In use, the test device, like other skin allergic test devices of prior type, is employed to press in contact with a skin portion of a patient, such as the arm skin, and then have its punctures brought into the epidermis layer (G) of the skin of a patient. A properly performed skin allergic test will leave a visible scarification which corresponds to the punctures thereof In the test process, a certain amount of antigen liquid loading onto punctures by the capillary phenomenon may be transferred to the test site of the epidermis layer of the skin of the patient. Finally, the test result may be properly interpreted about 20 minutes after the specific antigen liquid has been provided.

Although various conventional skin allergic test device of puncture type have provided the practitioners or technicians in the art with a convenient way in performing a skin allergic test, yet none of the conventional test devices can be performed to obtain correct and reproducible test result by a person who is not a medical practitioner, since the skin allergic test performed by any skin allergic test device of puncture type are required to meet the following test condition in order to obtain an accurate interpretation for the test result.

(1) the punctures of a skin allergic prick test device are not allowed to penetrate through the epidermis layer of the skin of a patient during the skin allergic test, as indicated in *Allergic Principles And Practice*, 3rd edition, P423–425, by Elliott et al.; and (2) the skin allergic test is required to be easily used by anyone with ordinary skill, therefore making the test data reproducible and assuring the reliability thereof.

However, the epidermis layer of human beings is extremely thin, it is therefore very likely for the epidermis layer of the skin to be penetrated through by the punctures of the test devices in the test process. As a result, the device as shown in FIGS. 1–3, should be operated by a medical practitioner or technician very skillful in the art in order to guarantee its reliability.

A disclosed skin allergic test device, U.S. Pat. No. 4,237,906 to Havstad et al., as shown in FIG. 3, describes an applicator or skin puncture test device having the flat end surface (E) which is provided at the end of the elongate stem (D), and a plurality of pointed projection (F) which are attached to the flat end surface (E), where the flat end surface (E) may be act as a stop to limit further penetration of the punctures in the test process.

Although the flat end surface (E) can be act as a stop to limit the depth of penetration, it is very difficult for such an applicator to be in the way that its punctures have the length of between about 0.1 mm to about 0.5 mm, so as to avoid excessive penetration of the punctures. Even though such a manufacturing difficulty may be overcome, the punctures thereof will be incapable of carrying sufficient antigen liquid, by its capillarity, so as to conduct the test.

SUMMARY OF INVENTION

Accordingly, it is the primary objective of the present invention to provide an improved quantitative skin allergic test device, which have at least a raised portion formed at the end of the elongated stem thereof for being act as a stop to limit excessive penetration of the punctures.

Other objective and merits and a further understanding of the present invention will be obtained by those having ordinary skill in the art when the following detailed description is read in conjunction with the accompanying drawings.

DRAWING FIGURES

DETAILED DESCRIPTION OF THE PREFERRED EMBODIMENT

Figure 4:
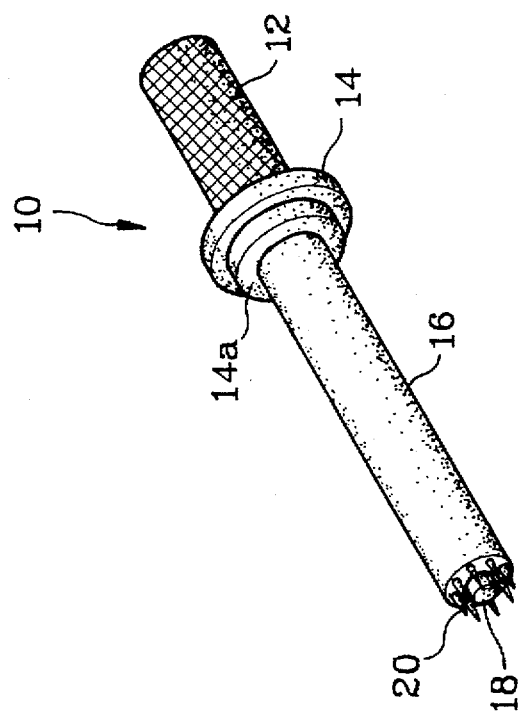
FIG. 4 is a perspective view of the skin allergic test device of the present invention.
Figure 9:
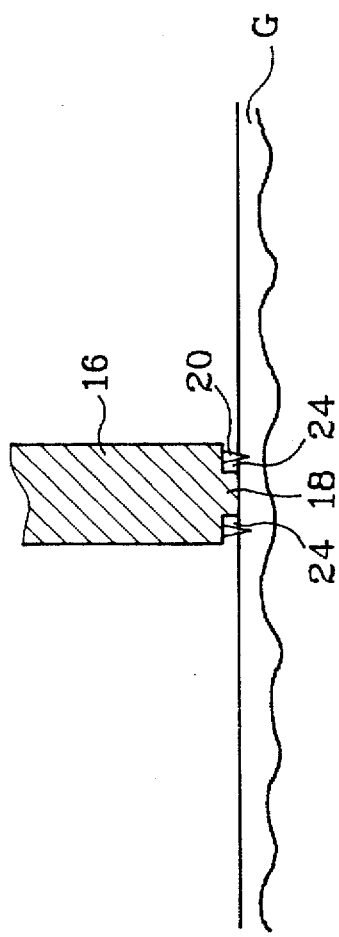
FIG. 9 is a sectional view of FIG. 6, which show the operating method of the present invention.

Please refer to FIG. 4, which shows the perspective view of the quantitative skin allergic test device (10) of the present invention. As shown in the figure, the quantitative skin allergic test device (10) of the present invention comprises a finger grip (12) to be held by fingers; a cover (14) provided at the bottom of the finger grip (12), which have a sealing plug portion (14a) adaptful to the mouth of a antigen container (22) (see FIG. 5); and an elongated stem extending downwardly from the sealing plug (14a), where there is a raised portion (18) formed at the end of the elongated stem (16) whereas there are a plurality of punctures (20), which are capable of carrying a certain amount of antigen liquid (24) by capillary phenomenon, provided around the raised portion (18) (see FIG. 6 and FIG. 9). As shown in FIG. 9, the punctures (20) are provided at the end of the elongated stem (16), substantially parallel to the axis of the raised portion (18) as well as the longitudinal axis of the elongated stem (16), and the punctures (20) each have a length greater than the height of the raised portion (18) by a predetermined value which is less than the thickness of the epidermis layer of the skin of human beings. Desirably, the length of each puncture (20) is designed to project out the raised portion

(18) by about 0.1 mm to about 0.5 mm, so that the epidermis layer of a patient will not be penetrated by the punctures (20) while conducting a skin allergic test since the raised portion (18) is act as a stop to limit excessive penetration of the punctures (20), which is the most important guideline that a technician or practitioner is required to obey in order to obtain an accurate interpretation of the test result and to make the test data reproducible and assure the test reliability.

Figure 3:
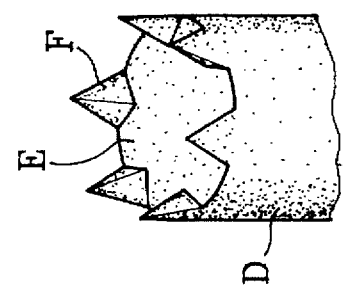
FIG. 3 is an enlarged fragmentary view of a conventional skin allergic test device.
Figure 2:
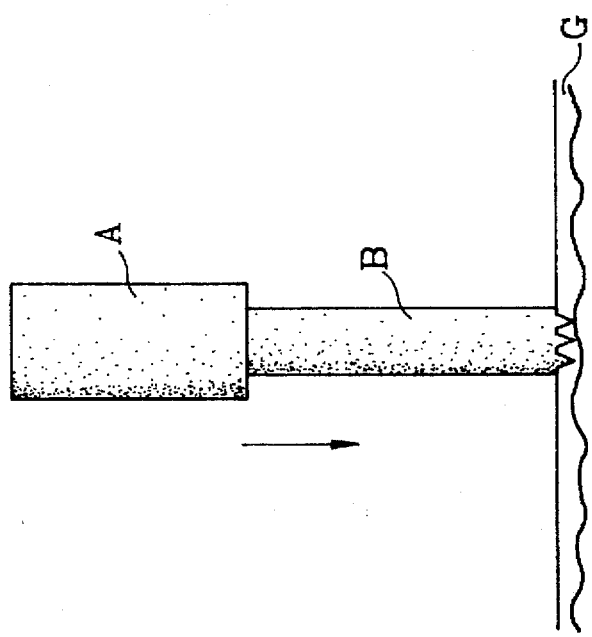
FIG. 2 shows the operating method of a conventional skin allergic test device of puncture type as shown in FIG. 1.
Figure 1:
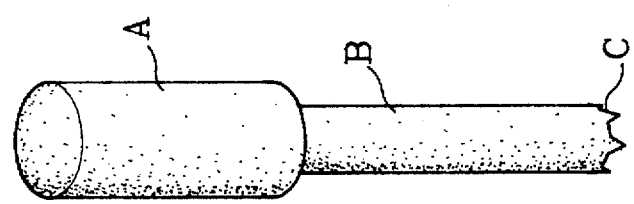
FIG. 1 shows a conventional skin allergic test device of puncture type.
Figure 5:
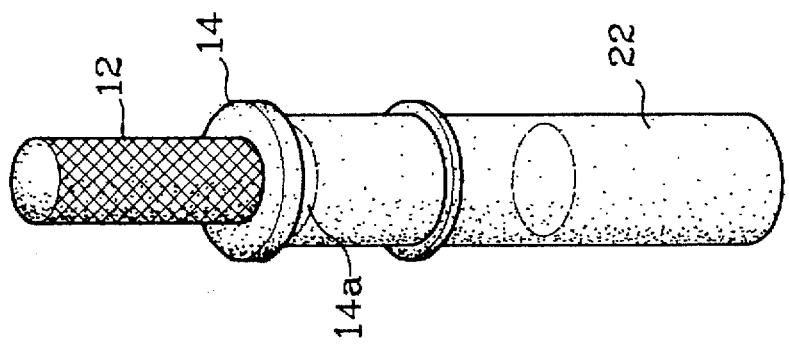
FIG. 5 shows the skin allergic test device of the present invention which has a cover and which is put in place with an antigen container, therefore preventing the antigen liquid therein from being contaminated.
Figure 6:
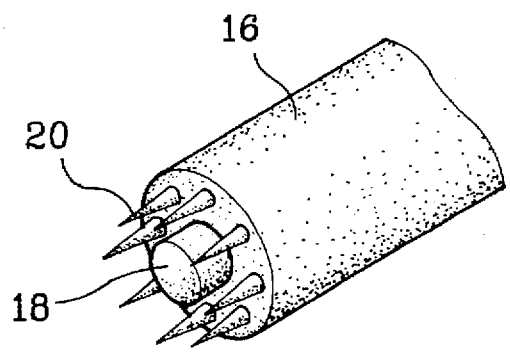
FIG. 6 is an enlarged fragmentary view of FIG. 5.

In use, a user may take a sterile skin allergic test device according to this invention, which is already loaded with a specific antigen liquid, by gripping the finger grip (12) thereof to have the punctures (20) in contact with the skin portion of a patient, such as the arm skin, and then have the punctures (20) brought into the epidermis layer of the skin to permit the antigen liquid adhered thereto to be transferred into the epidermis layer. As shown in the figure, since the punctures (20) are made to project out the raised portion (18) by a predetermined value which is less than the thickness of the epidermis layer of the skin, it is impossible that the punctures (20) can penetrate the epidermis layer when using the present device. Thus, the reliability concerning the interpretation of the skin allergic test result will be guaranteed. After finishing the test, the present device may be put in place with the antigen container. As can be seen in FIG. 5, the sealing plug portion (14a) of the cover (14) is in pressure seal with the mouth of the container (22),which may prevent the foreign materials from entering into the container (22) and prepare the next test.

Figure 7:
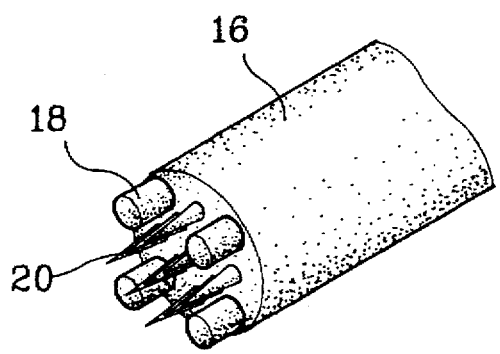
FIG. 7 is another embodiment of skin allergic test device according to the present invention.
Figure 8:
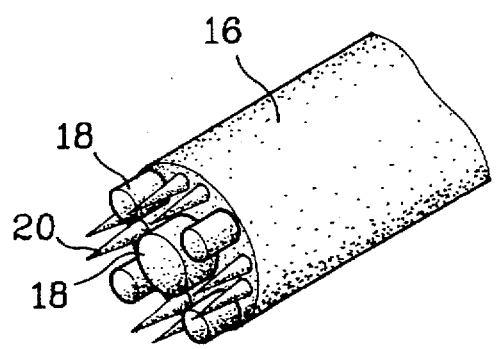
FIG. 8 is another embodiment of skin allergic test device according to the present invention.

FIG. 7 and FIG. 8 show alternative embodiments of the skin allergic test device according to the present invention, where the raised portions (18) are formed with different configurations and arrangements, and they are also act as stops to limit an over penetration. Although the raised portion (18) are in the form of the configurations and arrangements as shown in these figures, it is understood that various changes can be made thereto without departing the spirit and the purpose of this invention.

Figure 10:
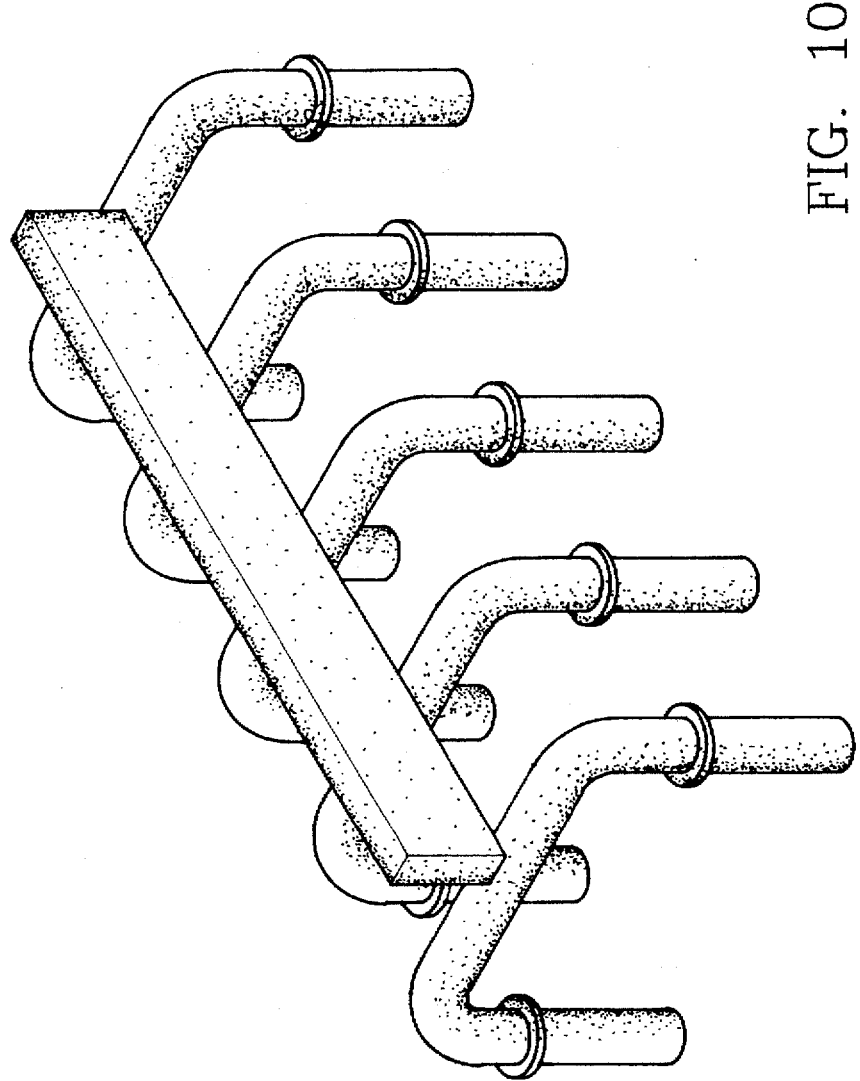
FIG. 10 is another embodiment of skin allergic test device according to the present invention.

Further, the present device is not only applied in a skin allergic test of sequential manner, as described in this disclosure, where each time only one skin test device, with a specific antigen liquid, is allowed to do the test; but also applied in a akin allergic test of simultaneous manner, as described in U.S. Pat. No. 3,556,080, issued in 1971, to Hein et al., where the present device can be provided at each leg of the disclosed multileg skin-testing device to assure its test reliability (see FIG. 10).

Although the present invention has been described with a certain degree of particularity, it is understood that the present disclosure is made by way of example only and that numerous changes in the detail of parts may be resorted to without departing the spirit and scope of the invention as hereinafter claimed.

I claim:

1. In a skin allergic test device of the type which includes a finger grip, an elongated stem extending therefrom, and a plurality of punctures provided at an end of said elongated stem, the improvement comprising:

the end of said elongated stem having at least a raised portion, which is in a spaced apart relationship with respect to said punctures so to act as a stop, each of said punctures extending from the end of said elongated stem, substantially parallel to the longitudinal axis of said elongated stem as well as the axis of said raised portion, and each said puncture having a length greater than the height of said raised portion by a predetermined value which is less than the thickness of the epidermis layer of human skin, so that each puncture will not penetrate through the epidermis layer of the skin of a patient due to said raised portion being acting as a stop during a skin allergic test, in order to obtain an accurate interpretation of the test result.

2. The improvement of claim 1, wherein said raised portion is substantially located at the center of the end of said elongated stem.

3. The improvement of claim 1, wherein said skin allergic test device further comprises a cover which has a sealing plug adaptful to the mouth of a antigen container to prevent the antigen liquid in said antigen container from being contaminated.

* * * * *